United States Patent [19]

Merger et al.

[11] Patent Number: 4,597,907

[45] Date of Patent: * Jul. 1, 1986

[54] PREPARATION OF α-SUBSTITUTED ACRYLAMIDES

[75] Inventors: Franz Merger, Frankenthal; Wolfgang Schwarz, Pfinztal, both of Fed. Rep. of Germany

[73] Assignee: BASF Aktiengesellschaft, Fed. Rep. of Germany

[*] Notice: The portion of the term of this patent subsequent to Jun. 10, 2003 has been disclaimed.

[21] Appl. No.: 677,309

[22] Filed: Dec. 3, 1984

[30] Foreign Application Priority Data

Dec. 2, 1983 [DE] Fed. Rep. of Germany ....... 3343675

[51] Int. Cl.⁴ .................. C11C 3/00; C07C 102/10
[52] U.S. Cl. .................... 260/404; 564/123; 564/204
[58] Field of Search ................. 564/123, 204; 260/404

[56] References Cited

U.S. PATENT DOCUMENTS 3,105,741 10/1963 Moore, Jr. .......................... 23/190
4,365,092 12/1982 Harwell et al. .................... 564/204

FOREIGN PATENT DOCUMENTS 0058927  9/1982  European Pat. Off. ............ 564/123
1044795 12/1955  Fed. Rep. of Germany .
1081884  2/1959  Fed. Rep. of Germany .
3205946  9/1983  Fed. Rep. of Germany ...... 564/123
 128302  4/1976  Japan ................................. 564/123

OTHER PUBLICATIONS

J. Am. Chem. Soc. 83, (1961), 1983.
Rec. Trav. Chim. Pays Bas 95, (1976) 123.

Primary Examiner—Charles F. Warren
Assistant Examiner—Carolyn S. Greason
Attorney, Agent, or Firm—Keil & Weinkauf

[57] ABSTRACT

α-substituted acrylamides of the general formula I

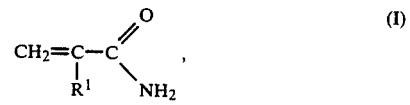

where $R^1$ is a straight-chain, branched or cyclic alkyl radical of not more than 15 carbon atoms which can be unsubstituted or further substituted, are prepared by a process in which the corresponding α-substituted acrolein oximes are heated at from 40° to 250° C. in the presence of a copper(II) carboxylate.

6 Claims, 1 Drawing Figure

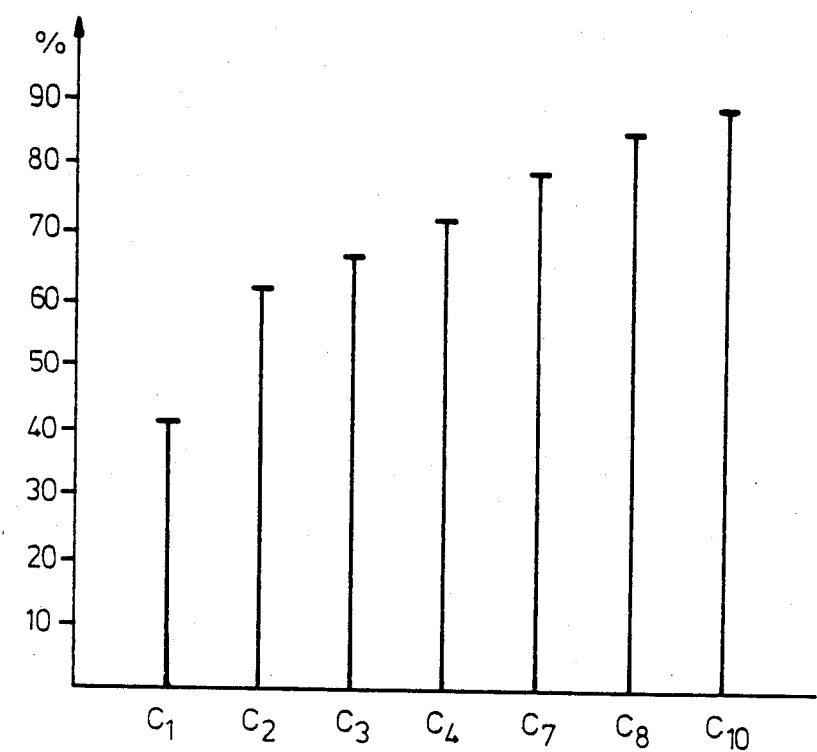

PREPARATION OF α-SUBSTITUTED ACRYLAMIDES

The present invention relates to a novel process for the preparation of α-substituted acrylamides starting from oximes of α-substituted acroleins.

α-substituted acrylamides can be obtained by amidation of the particular esters with ammonia, or by hydration of the corresponding nitriles. However, only a limited number of the acrylates and acrylonitriles required for this purpose can be synthesized, the synthesis essentially being restricted to the (meth)acrylyl compounds. Moreover, the amidation is technically complicated and does not take place particularly selectively, since side reactions, such as Michael addition reactions, can occur.

U.S. Pat. No. 4,365,092 proposes the preparation of methacrylamide from methyl methacrylate using aqueous ammonia solution. However, this procedure requires long reaction times and relatively large amounts of expensive anionic surfactants, which make the isolation and purification of the amide more difficult.

Another route for synthesizing methacrylamide starts from acetone cyanohydrin, methacrylamide sulfate being an intermediate. However, this procedure produces large amounts of salts, and expensive purification steps also have to be carried out.

The literature also discloses that acid amides can be prepared by rearrangement reactions of aldoximes (J.Am.Chem.Soc. 83, (1961), 1983 and Rec.Trav.Chim.-Pays Bas 95, (1976), 123, and 96 (1977), 142). The aldehydes on which the aldoximes are based generally belong to the class consisting of the saturated or the aromatic aldehydes. The catalysts used are salts of nickel, zinc, palladium, cobalt or copper. Nickel(II) acetate and palladium(II) acetate have proven particularly effective, whereas, in the case of benzaldoxime, copper(II) acetate results in undesirable reactions or gives poor yields.

In addition to the rearrangement of saturated aldoximes and benzaldoximes, JP-A-128 302/1977 also describes the conversion of cinnamaldehyde oxime in the presence of copper acetylacetonate. However, we have found that the use of this complex in the preparation of α-alkyl-substituted acrylamides does not lead to satisfactory results.

Finally, DE-A-3 205 946 proposes the preparation of methacrylamide starting from methacrolein oxime, in the presence of a catalyst based on copper/chromium. This catalyst advantageously should be used in the form of a supported catalyst and must have a defined molar ratio of copper to chromium.

However, the yield of methacrylamide in this process is only 72%. Moreover, we have found that none of the copper salts stated therein give the desired optimum results when used, these salts constituting the copper component of the catalyst and being derived from formic acid, acetic acid and tartaric acid.

In view of the fact that the syntheses disclosed to data for α-alkyl-substituted acrylamides are unsatisfactory and generally restricted to methacrylamide, it is an object of the present invention to prepare such compounds in a simpler and more economical manner.

We have found that this object is achieved, and that, accordingly, α-substituted acrylamides of the general formula I

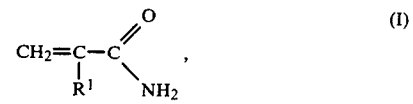

where $R^1$ is a straight-chain, branched or cyclic alkyl radical of not more than 15 carbon atoms which can be unsubstituted or further substituted, are advantageously obtained from the aldoximes of the general formula II

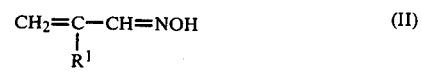

where $R^1$ has the above meaning, if the aldoxime is heated at from 40° to 250° C. in the presence of a carrier-free copper(II) carboxylate obtained from a monocarboxylic acid of 5 to 18 carbon atoms.

The novel process is carried out using oximes of acroleins which carry a straight-chain, branched or cyclic alkyl radical of not more than 15 carbon atoms in the α-position. This alkyl radical can be substituted by further groups which are inert under the reaction conditions, for example lower alkoxy (also in the geminal position), lower acyloxy, lower alkoxycarbonyl or lower mono- or dialkylamino groups.

Examples of α-alkyl-substituted acrolein oximes are α-methacrolein oxime, α-ethylacrolein oxime, α-butylacrolein oxime, α-(2-ethylhexyl)-acrolein oxime, α-nonylacrolein oxime, α-cyclohexylacrolein oxime, α-(4-methylcyclohexyl)-acrolein oxime, α-(3-carbethoxypropyl)-acrolein oxime and α-(4,4-dimethylaminobutyl)-acrolein oxime.

The α-substituted acroleins from which the aldoximes (II) are derived can readily be obtained by means of the process described in EP-A-58 927, by reaction of an alkanal with formaldehyde and a secondary amine in the presence of an acid.

The aldoximes required for the noval process can be prepared from the α-substituted acroleins and hydroxylammonium salts by a conventional method, as described in, for example, Houben Weyl, Methoden der organischen Chemie, volume 10/4, page 55 et seq., the acid liberated being neutralized with a base.

We have furthermore found that, in the preparation of the lower homologs of these aldoximes, in which the unsubstituted or substituted α-alkyl radical is of not more than 4 carbon atoms, the usual addition of a base can, surprisingly, be dispensed with. Formation and isolation of the aldoximes take place without neutralization of the acid and corresponding salt formation. The aqueous acid can be recycled, or used for neutralization purposes.

Technical-grade aqueous hydroxylammonium salt solutions can advantageously be used. Excess acid and its ammonium salts, as are present in such technical-grade solutions, do not present problems.

The rearrangement reaction of the aldoxime to give the corresponding α-substituted acrylamide is carried out at from 40° to 250° C., preferably from 60° to 180° C., in particular from 80° to 150° C.

The reaction is preferably carried out under atmospheric pressure, but in some cases it is advantageous to employ superatmospheric pressure of not more than 20 bar.

The reaction can be carried out in the absence of a solvent but is preferably carried out in the presence of an inert solvent, such as toluene, xylene, mesitylene, chlorobenzene, nitrobenzene, tetralin, decalin, dioxane, dibutyl ether or n-butyl acetate.

According to the invention, the rearrangement reaction of the aldoximes is carried out in the presence of a carrier-free copper(II) carboxylate obtained from a monocarboxylic acid of 5 to 18, preferably 6 to 12, in particular 6 to 10, carbon atoms.

Examples of suitable acids of this type are unsubstituted or substituted monocarboxylic acids containing a saturated or unsaturated straight-chain, branched or cyclic alkyl radical, aralkanoic acids, oxaalkanoic acid and aromatic carboxylic acids, eg. 2-methylbutanoic acid, pentanoic acid, hexanoic acid, 2-ethylhanoic acid, 3,5,5-trimethylhexanoic acid, decanoic acid, 9-decanoic acid, 9-dodecenoic acid, 9-octadecenoic acid, cyclohexanecarboxylic acid, phenylacetic acid, 1-phenylcyclopentane-1-carboxylic acid, methoxyacetic acid, benzoic acid, 3,5-dichlorobenzoic acid or naphthoic acid.

It has proven particularly advantageous to carry out the reaction in the presence of the copper(II) salt of 2-ethylhexanoic acid or of decanoic acid.

We have found that copper salts of monocarboxylic acids containing a relatively large number of carbon atoms are more effective than salts of carboxylic acids containing a smaller number of carbon atoms (cf. the drawing).

This systematic effect which is specific to the process according to the invention was not evident from the findings to date concerning the rearrangement of saturated or aromatic aldoximes, since, in the case of the rearrangement of benzaldoxime the use of nickel(II) formate on the one hand and nickel(II) acetate on the other hand gave identical results (JP-A-128 302/1977).

The copper salts required for the process according to the invention can be prepared by a conventional method, for example by reacting the carboxylic acid with copper(II) carbonate, or by reacting a copper salt with an alkali metal or ammonium salt of the particular carboxylic acid.

The copper salts are used in a carrier-free form, ie. without a carrier frequently used in catalyst technology, and are advantageously employed in the absence of chromium.

The amount of the copper(II) carboxylate used is from 0.5 to 50, preferably from 2 to 10, in particular from 3 to 6, mol %, based in each case on 1 mole of aldoxime.

The novel process is usually carried out as follows: the aldoxime together with the copper(II) carboxylate, preferably in an inert solvent, is heated to the stated temperature, either a batchwise or a continuous procedure being possible. To permit the exothermic reaction to be controlled more readily, it is advantageous initially to take only some of the oxime, and to add the remainder in the course of the reaction.

When the reaction is complete, the desired products are isolated by crystallization or extraction, and can be used directly for many purposes. They can be purified by recrystallization, and, if desired, can be freed from traces of copper by ion exchange.

Particular advantages of the novel process are the use of the acroleins, which are readily obtainable compared with the acrylates and are frequently used as intermediates for the synthesis of these, and the fact that the aldoxime rearrangement takes place particularly selectively under the reaction conditions.

The amides obtained by the process according to the invention are useful intermediates for the preparation of modifiable polymers, for example for dispersions and surface coatings.

The Examples which follow illustrate the invention.

EXAMPLE 1

Preparation of methacrolein oxime 370 g of 98% pure methacrolein were added dropwise, at about 3° C. and in the course of 1 hour, to 1510 ml of a vigorously stirred solution containing 490.3 g of hydroxylammonium sulfate, 19.25 g of sulfuric acid and 30.83 g of ammonium sulfate. Cooling was then discontinued and the mixture was stirred for a further 2 hours, the temperature of the reaction mixture increasing to 21° C. Analysis by gas chromatography showed that 97% of the methacrolein had been converted. The organic phase was separated off, the aqueous phase was extracted twice with ether, the combined organic phases were dried over magnesium sulfate and evaporated down in a rotary evaporator, and the residue was distilled in a thin-film evaporator (82° C./16 mbar). 387 g (yield 90%, based on methacrolein converted) of 99.6% pure methacrolein oxime were obtained.

EXAMPLE 2

20 g of methacrolein oxime, 6 mol % (based on oxime) of Cu(II) carboxylate (cf. Table), and 13.35 g of diphenyl ether (internal standard) in 120 g of o-xylene were heated at 110° C., while stirring, and an exothermic reaction began. When this reaction had died down, the mixture was allowed to continue reacting at 110° C., until all of the oxime had been consumed (gas chromatography). The yields stated are based on quantitative gas chromatographic analyses using an internal standard. The reactions (a) to (f) serve for comparison.

TABLE

| Cu(II) carboxylate | Reaction time (hour) | Yield of amide (%) |
| --- | --- | --- |
| (a) Cu formate | 10 | 41 |
| (b) Cu acetate | 5 | 62 |
| (c) Cu propionate | 1 | 67 |
| (d) Cu butyrate | 1 | 72 |
| (e) Cu tartrate | 4 | 0 |
| (f) Cu acetylacetonate | 4 | 58 |
| (g) Cu heptanoate | 1 | 79 |
| (h) Cu 2-ethylhexanoate | 1 | 85 |
| (j) Cu decanoate | 1 | 89 |

EXAMPLE 3

Preparation of ethylacrolein oxime 414 g of 98.5% pure ethylacrolein were added dropwise, at 25° C. and in the course of 8 minutes, to 2.7 l of a vigorously stirred solution containing 459.7 g of hydroxylammonium sulfate, 18.1 g of free sulfuric acid, and 46.2 g of ammonium sulfate. Stirring was then continued for 2.5 hours at 25° C., after which the phases were separated, the aqueous phase was extracted by shaking with chloroform, and the combined organic phases were dried over sodium sulfate and evaporated down in a rotary evaporator. Distillation in a thin-film evaporator (105° C./32 mbar) gave 436 g (95%) of ethylacrolein oxime.

EXAMPLE 4

(Comparison)

23.3 g of ethylacrolein oxime and 6 mol % (based on oxime) of Cu(II) acetate in 120 g of xylene were heated at 110° C. When the exothermic reaction had died down, stirring was continued at 110° C., the reaction being complete after one hour. The mixture was evaporated down in a rotary evaporator, and the residue was taken up in 250 ml of petroleum ether and 5 ml of methanol. The crude ethylacrylamide precipitated on cooling to −20° C. was filtered off under suction and dried. Yield: 16.5 g (70.8%).

EXAMPLE 5

The procedure was carried out similarly to that described in Example 4, but 6 mol % of Cu(II) 2-ethylhexanoate were used instead of 6 mol % of Cu(II) acetate. Yield: 18.9 g (81.1%).

EXAMPLE 6

403 g of α-(3-carbethoxypropyl)-acrolein oxime were added, in the course of 15 minutes, to a boiling solution of 49.4 g (6 mol %, based on oxime) of Cu(II) 2-ethylhexanoate in 1200 g of o-xylene. When the addition was complete, the mixture was refluxed for a further 10 minutes, after which it was cooled to −20° C., the crude amide precipitated was taken up in 1.5 l of water, the aqueous solution was poured onto an acidic synthetic resin ion exchanger, and the solution obtained was evaporated down in a rotary evaporator to give 317 g (77%) of a pale yellow liquid, which crystallized completely when seeded. Mp.: 48° C. (from toluene).

We claim:

1. A process for the preparation of an α-substituted acrylamide of the formula I

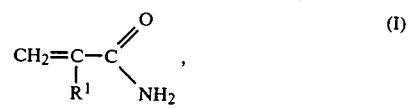

where $R^1$ is a straight-chain, branched or cyclic alkyl radical of not more than 15 carbon atoms which can be unsubstituted or further substituted, from an aldoxime of the formula II

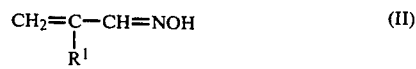

where $R^1$ has the above meaning, wherein the aldoxime is heated at from 40° to 250° C. in the presence of a carrier-free copper(II) carboxylate obtained from a monocarboxylic acid of 5 to 18 carbon atoms.

2. The process of claim 1, wherein the reaction is carried out at from 60° to 180° C.

3. The process of claim 1, wherein the reaction is carried out in the presence of a copper(II) carboxylate obtained from a monocarboxylic acid 6 to 12 carbon atoms.

4. The process of claim 1, wherein the reaction is carried out in the presence of a copper(II) carboxylate obtained from a monocarboxylic acid of from 6 to 10 carbon atoms.

5. The process of claim 1, wherein the reaction is carried out under atmospheric pressure.

6. The process of claim 1, wherein the reaction is carried out in the presence of an inert solvent.

* * * * *